(12) United States Patent
Palmer

(10) Patent No.: US 10,912,918 B1
(45) Date of Patent: Feb. 9, 2021

(54) PRE-LUBRICATED FEMALE URINARY CATHETER PACKAGE

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 0 days.

(21) Appl. No.: 16/827,276

(22) Filed: Mar. 23, 2020

(51) Int. Cl.
*A61M 25/00* (2006.01)
*A61M 25/01* (2006.01)

(52) U.S. Cl.
CPC ...... *A61M 25/002* (2013.01); *A61M 25/0017* (2013.01); *A61M 25/0111* (2013.01); *A61M 2210/1092* (2013.01)

(58) Field of Classification Search
CPC ............ A61M 25/002; A61M 25/0017; A61M 25/0111; A61M 2210/1092; A61M 5/344; A61M 2039/0229; B65D 41/00; B65D 43/00
See application file for complete search history.

(56) References Cited

U.S. PATENT DOCUMENTS

| | | |
|---|---|---|
| 3,114,455 A | 12/1963 | Claisse et al. |
| 3,149,717 A | 9/1964 | Castelli |
| 3,229,813 A | 1/1966 | Crowe et al. |
| 3,861,395 A | 1/1975 | Tokudo |
| 3,967,728 A | 7/1976 | Gordan et al. |
| 4,479,586 A * | 10/1984 | Csaszar ............ B65D 41/3452 215/258 |
| 4,622,033 A | 11/1986 | Taniguchi |
| 4,696,296 A * | 9/1987 | Palmer ............ A61M 16/0463 128/207.16 |
| 4,811,847 A | 3/1989 | Reif et al. |
| 5,669,931 A * | 9/1997 | Kupiecki ......... A61B 17/12022 606/191 |
| 5,792,114 A * | 8/1998 | Fiore ................. A61M 25/0111 604/171 |
| 6,053,905 A | 4/2000 | Daignault et al. |
| 6,090,075 A * | 7/2000 | House ............. A61M 25/0017 604/172 |
| 6,578,709 B1 | 6/2003 | Kavanahg et al. |
| 6,602,244 B2 | 8/2003 | Kavanahg et al. |

(Continued)

FOREIGN PATENT DOCUMENTS

| | | |
|---|---|---|
| WO | 03008028 A2 | 1/2003 |
| WO | 012060699 A1 | 5/2012 |

*Primary Examiner* — Adam Marcetich
(74) *Attorney, Agent, or Firm* — SoCal IP Law Group LLP; Guy Cumberbatch; Steven C. Sereboff

(57) ABSTRACT

A rigid package or container for a sterile pre-lubricated, ready to use female-length catheter with enhanced gel receptacles and simple constructions. A main body of the rigid container has a hollow interior which may receive a gel receptacle defining an inner cavity filled with a lubricating gel. The gel receptacle partly inserts into the main body and a tube of the catheter inserts through the gel receptacle into the main body with a proximal outlet projecting out of the gel receptacle so as to be graspable. Alternatively, the gel may be provided within the hollow interior of the main body. A rigid and closed cap seals to either the main body or the gel receptacle and closes the hollow interior of the main body.

19 Claims, 14 Drawing Sheets

(56) References Cited

U.S. PATENT DOCUMENTS

| | | | |
|---|---|---|---|
| 6,634,498 B2 | 10/2003 | Kayerod et al. | |
| 6,638,269 B2 | 10/2003 | Wilcox | |
| 8,181,778 B1 | 5/2012 | van Groningen et al. | |
| 8,317,775 B2 | 11/2012 | House | |
| 8,579,115 B2 | 11/2013 | Murphy et al. | |
| 8,668,683 B2 | 3/2014 | Golden | |
| 9,220,866 B2 | 12/2015 | van Groningen et al. | |
| 9,687,629 B1 | 6/2017 | Palmer | |
| 2004/0055926 A1* | 3/2004 | Duffy | A61M 25/002 206/571 |
| 2006/0263404 A1 | 11/2006 | Nielsen et al. | |
| 2008/0172042 A1 | 7/2008 | House | |
| 2008/0183191 A1 | 7/2008 | Tracy et al. | |
| 2009/0008279 A1* | 1/2009 | Tanghoej | A61M 25/002 206/364 |
| 2009/0024111 A1* | 1/2009 | Borodulin | A61M 25/0111 604/544 |
| 2012/0110951 A1* | 5/2012 | van Groningen | A61M 25/0111 53/425 |
| 2013/0245496 A1* | 9/2013 | Wells | A61F 5/4405 600/581 |
| 2015/0018803 A1* | 1/2015 | Tjassens | A61M 25/002 604/544 |
| 2017/0056622 A1* | 3/2017 | O'Flynn | A61M 25/0017 |
| 2017/0080177 A1* | 3/2017 | Tanghoej | A61M 25/0111 |
| 2017/0173300 A1* | 6/2017 | Hannon | B65D 55/16 |
| 2018/0161539 A1* | 6/2018 | Palmer | A61L 29/06 |
| 2019/0126004 A1* | 5/2019 | O'Brien | A61M 25/002 |
| 2019/0151605 A1* | 5/2019 | McMenamin | B65D 43/162 |

\* cited by examiner

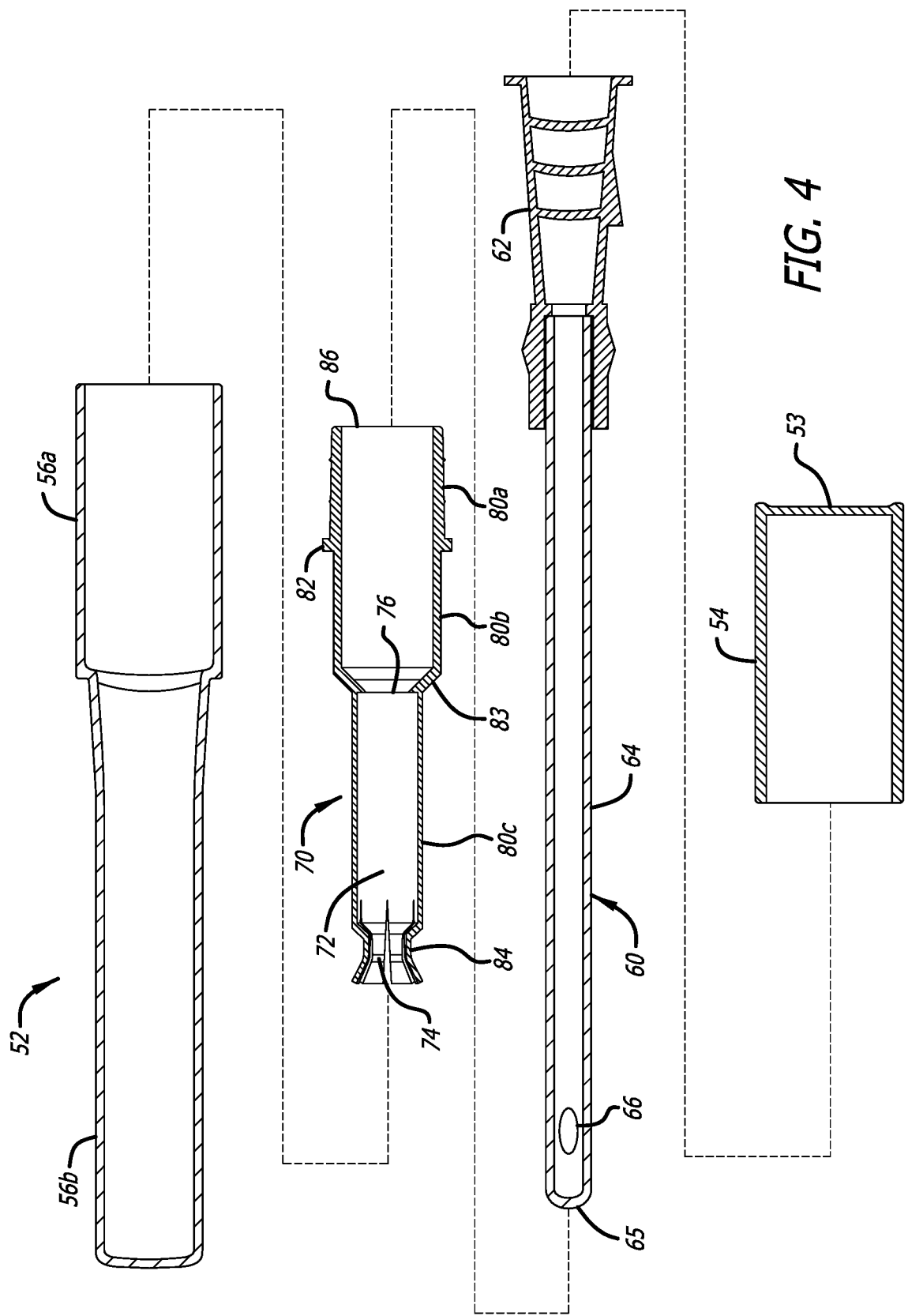

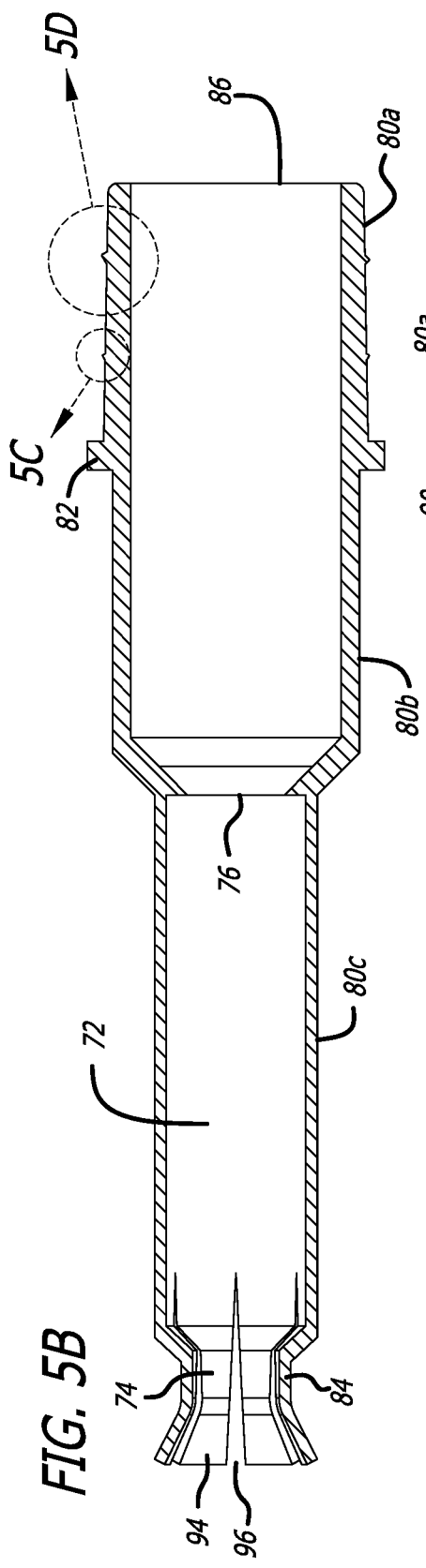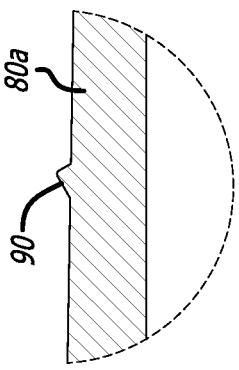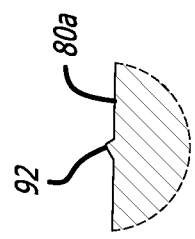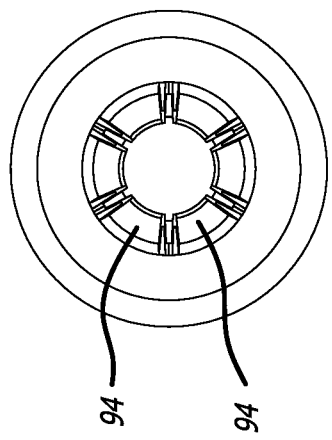

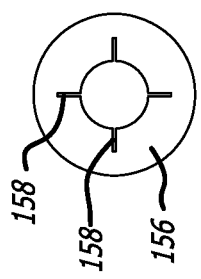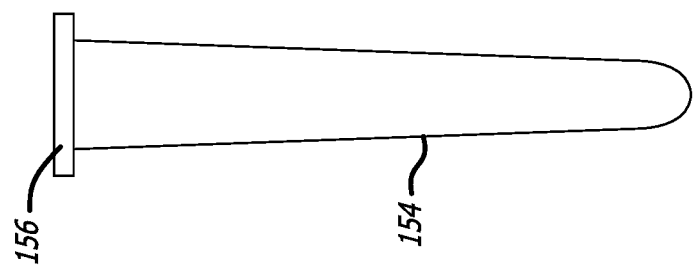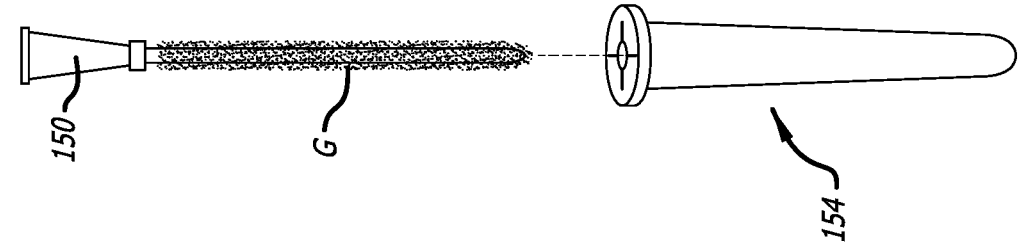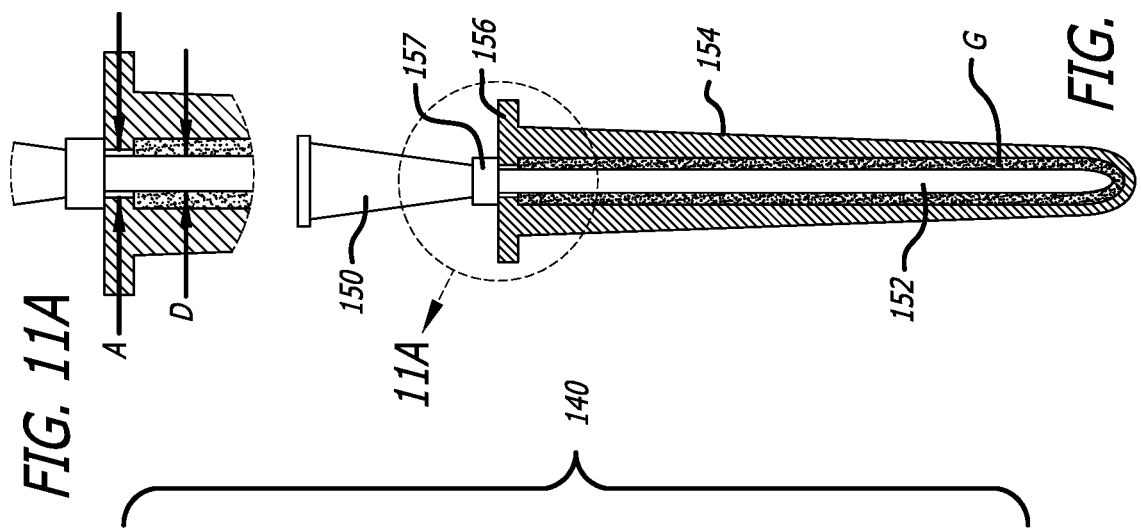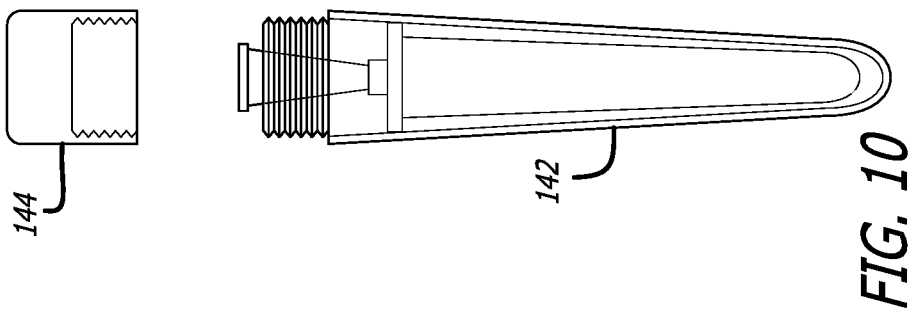

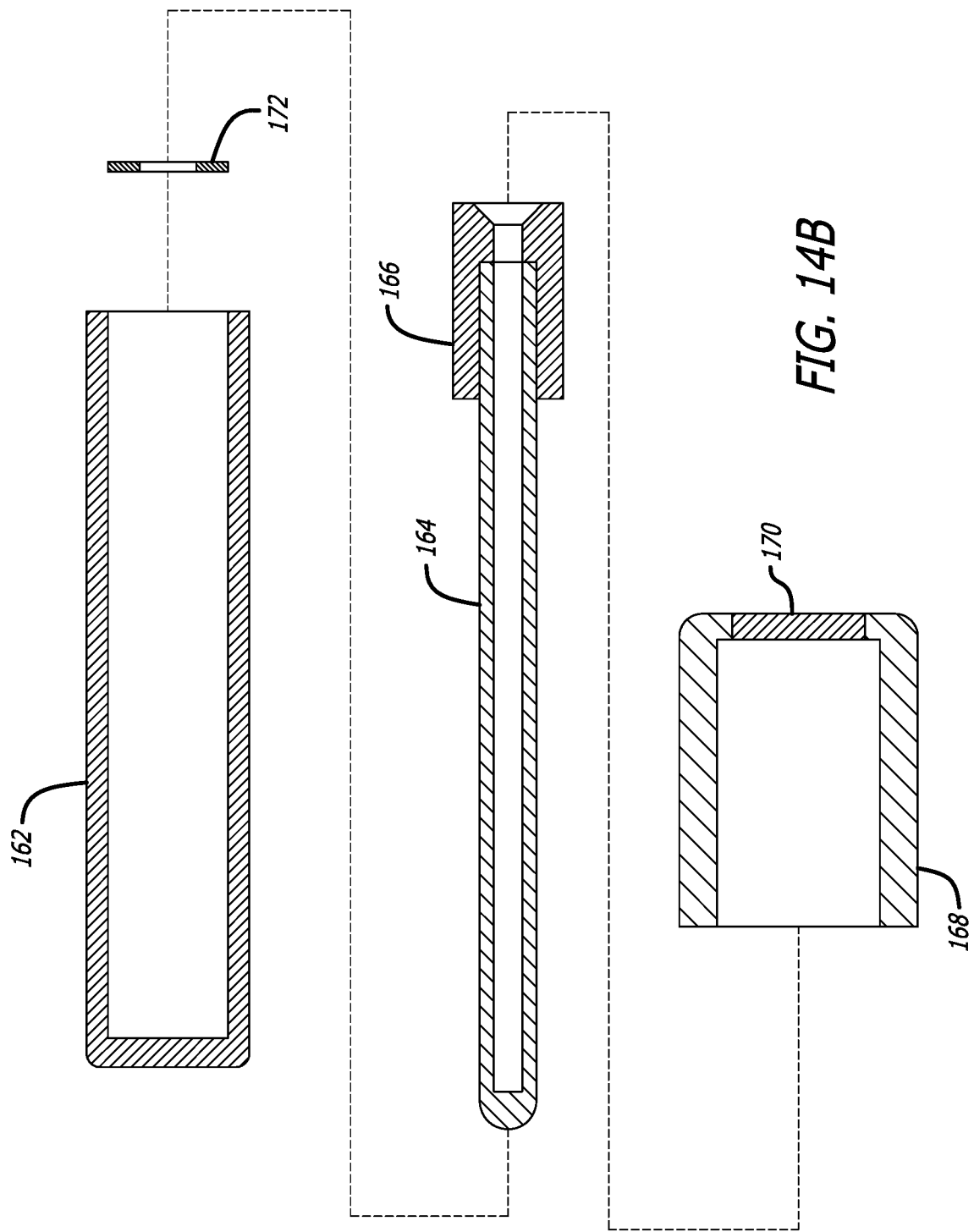

US 10,912,918 B1

PRE-LUBRICATED FEMALE URINARY CATHETER PACKAGE

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner have no objection to the facsimile reproduction by anyone of the patent disclosure as it appears in the Patent and Trademark Office patent files or records, but otherwise reserves all copyright and trade dress rights whatsoever.

FIELD

The present application relates to a sterile rigid package housing a female pre-lubricated urinary catheter which can be used for (intermittent) self-catheterization by a patient.

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need, single use catheters have been developed to allow patients to perform self-catheterization.

A gel container is used as a means to apply gel to a urinary catheter upon withdrawal of the catheter from a package. Typically, the gel container is made of a flexible material like molded silicone. If the container is assembled into a rigid package there is no way for the user to manipulate the container to ensure adequate gel coverage of the distal (tip) end of the catheter.

Urinary catheters come in different lengths depending on the user: There are conventionally three lengths: female (12-26 cm), standard for men (40-45 cm) and pediatric (30-31 cm).

The Cure Twist available from Cure Medical of Newport Beach, Calif. is a compact female length catheter packaged in a rigid tube package with an internal, flexible gel receptacle molded of silicone rubber. To help reduce the stigma of having to use the catheter, the Twist package is relatively short and conveniently resembles a tube for cosmetics, such as eyeliner. The gel receptacle holds lubricating gel in storage and applies it to the catheter tubing as the catheter is withdrawn from the package. U.S. Pat. No. 8,181,778 discloses such a rigid container for a catheter having a shortened tube with a leading end and a proximal end provided with a catheter outlet or connector. U.S. Pat. No. 9,687,629 discloses alternative gel receptacles which are shaped so as to ensure gel covers the extreme distal tip of the catheter. The user removes the catheter for use, either by joining the connector to a collection bag or other collection device or by simply using the catheter while sitting on the toilet. The catheter is lubricated and ready to use directly from the package.

Though the Cure Twist packaged catheter is convenient and surreptitious, it includes a number of components that raise its price, and thus there is a need for a similar product which is simpler and thus less expensive to make.

SUMMARY OF THE INVENTION

Embodiments of the present invention seek to provide an enhanced package for a urinary catheter, suitable for everyday use by a patient.

In one embodiment, a package or container consists essentially of a rigid generally tubular main body, a urinary catheter and a rigid cap. The main body has a distal closed end and a proximal open mouth and defines within a hollow interior. The urinary catheter has an elongated flexible tube defining a closed distal tip with one or more flow openings formed in an adjacent sidewall thereof, and a proximal outlet attached to a proximal end of the tube and having a throughbore in communication with a lumen of the tube. The tube of the urinary catheter is inserted through the open mouth of the main body and into the hollow interior such that at least a portion of the outlet remains outside the main body. An outer diameter of the tube is less than an inner diameter of the hollow interior so that a concentric space is formed therebetween which is at least partly filled with a lubricating gel to the distal closed end of the main body such that lubricating gel remains on the catheter tube when the tube is retracted from within the main body. The rigid cap secures to the open mouth of the main body, and the rigid cap is solid without openings so as to seal the urinary catheter within the hollow interior in a sterile manner.

The rigid cap is preferably secured to the open mouth of the main body with mating threads. The generally tubular main body may have a shallow hourglass shape that narrows in a middle portion and the lubricating gel is deposited only in a distal end of the hollow interior of the main body to limit the amount of gel that remains on the catheter tube when retracted from within the main body.

The urinary catheter package may further including a divider wall secured within the main body and having a central aperture sized slightly larger than the catheter tube. The divider wall segregates the hollow interior of the main body into a proximal first section and a distal second section, wherein the lubricating gel is deposited only in the distal second section. A diameter D of the catheter tube preferably ranges between about 2.7-5.3 mm, and a diameter A of the central aperture is about 1-2 mm larger than the diameter D. The divider wall may be formed by a molded bulkhead within the main body, or may be a removable annular disk retained within the inside of the main body with adhesive or held in place by a snap fit into a ring-shaped receiving cavity.

A second embodiment of urinary package or container consists essentially of a rigid generally tubular main body, a gel receptacle, a urinary catheter and a rigid cap. The main body has a distal closed end and a proximal open mouth and defining within a hollow interior. The gel receptacle has a distal section defining an inner cavity at least partly filled with a lubricating gel and a proximal section. The distal section has a distal opening and a proximal opening leading to the proximal section, and the proximal section has an open proximal end. The gel receptacle is inserted through the open mouth of the main body and into the hollow interior, and the gel receptacle has an outer circumferential rib at one end of the proximal section that is sized to interfere with the open mouth such that the proximal section remains outside the hollow interior of the main body. The urinary catheter has an elongated flexible tube defining a closed distal tip with one or more flow openings formed in an adjacent sidewall thereof, and a proximal outlet attached to a proximal end of the tube and having a throughbore in communication with a lumen of the tube. The tube of the urinary catheter is inserted first into the open proximal end of the proximal section and extends through the entire gel receptacle such that the distal tip extends past the distal opening of the distal section and is within the hollow interior of the main body and at least a portion of the outlet remains outside the main body. A concentric space is formed around the tube within the distal section of the gel receptacle such that lubricating gel remains on the catheter tube when the tube is retracted from within the gel receptacle. The rigid cap secures to the proximal section of the gel receptacle, the rigid cap being solid without openings so as to seal the urinary catheter within the hollow interior in a sterile manner.

The package of the second embodiment may further include a gel cap filled with gel that fits over the distal tip of the catheter tube, the gel cap being larger than the distal opening of the distal section so that it falls off the end of the tube when the tube is retracted from within the gel receptacle. The gel cap may have a hemispherical cup-shaped body and an outer flange that is larger than the distal opening of the distal section. The distal opening of the distal section of the gel receptacle may be defined by a plurality of cantilevered fingers separated by longitudinal slots, and the gel receptacle is molded of a flexible polymer which permits introduction of the lubricant gel into the inner cavity by inserting a syringe or other similar implement between the catheter tube and the cantilevered fingers which flex outward. The longitudinal slots preferably commence along the distal section and gradually widen toward the distal ends of the cantilevered fingers. The urinary catheter package of claim 12, wherein the cantilevered fingers are molded to constrict a distal end of the distal section, then extend a short linear distance within which is defined the distal opening, before flaring outward to distal ends of the cantilevered fingers.

The proximal section of the gel receptacle may have a diameter that is approximately the same as an inner luminal diameter of the rigid cap such that the rigid cap is secured to the proximal section with an interference fit. The proximal section may have a pair of external axially-spaced ribs that interfere with the inner luminal diameter of the rigid cap so as to retain and seal it on the proximal section. In one embodiment, the proximal section is molded with a slight narrowing taper toward the proximal opening and a proximal rib is sized larger than a distal rib so as to have about the same diameter. The ribs may be triangular and asymmetric in cross-section with a steeper proximal face than a distal face.

The catheter of either embodiment may have a length of between about 10-15 cm, and the catheter package has a length of no more than 1-2 cm longer than the catheter.

BRIEF DESCRIPTION OF THE DRAWINGS

FIG. 4 is an exploded view of the components thereof;

FIG. 10 is a side elevational view of an alternative sterile container for an intermittent urinary catheter;

FIG. 11 is a sectional view through a gel receptacle which receives a catheter tube for use in the sterile container of FIG. 10, and FIG. 11A is an enlarged view of an open end of the gel receptacle and catheter;

FIG. 12 is an exploded view of the catheter tube removed from the gel receptacle of FIG. 12 showing complete coverage of the catheter tube with lubricant gel;

FIGS. 13A and 13B are orthogonal views of the gel receptacle of FIG. 12;

FIGS. 14A-14B are exploded views of alternative configurations of the components of the sterile container of FIG. 14.

DETAILED DESCRIPTION OF A PREFERRED EMBODIMENT

The present application provides an easy to use and easy to carry solution for providing a medical device in the form of a catheter.

Figure 1:
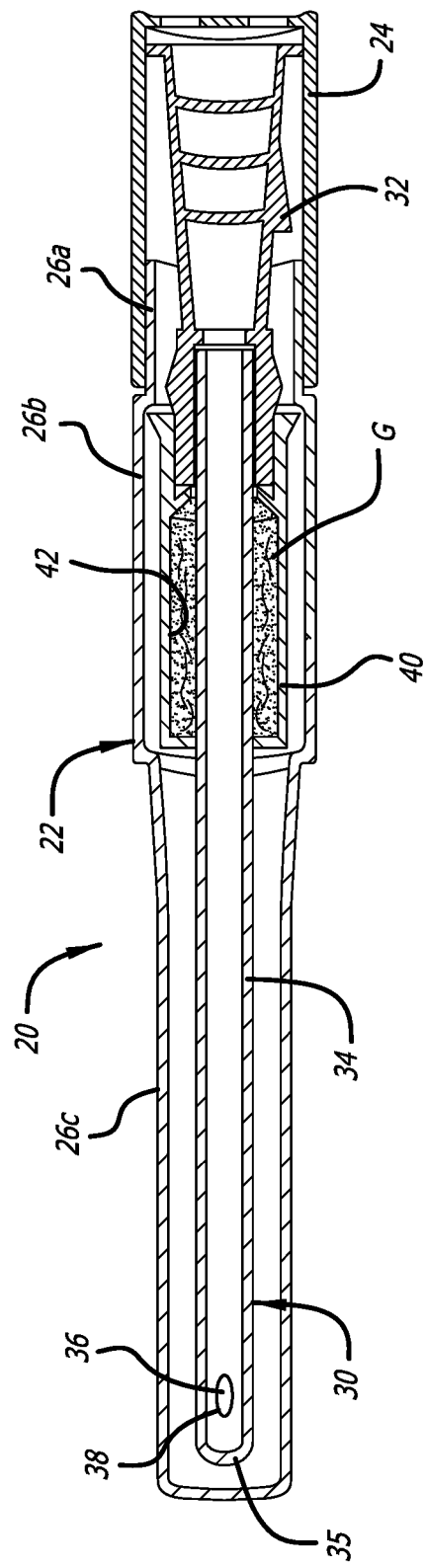
FIG. 1 is a longitudinal sectional view through a sterile container of the prior art for an intermittent urinary catheter.

FIG. 1 illustrates a cross sectional view of a prior art intermittent catheter container 20 such as shown in U.S. Pat. No. 8,181,778, with all elements assembled. Catheter container 20 includes a pen-like rigid and generally hollow tubular main body 22 which is closed off at a distal end 23 thereof, and which can be closed off at a proximal, open end using a cap 24.

The cross-sectional view of main body 22 shows a proximal first part 26$a$, a middle second part 26$b$ and distal third part 26$c$, which have respective diameters as described in U.S. Pat. No. 8,181,778. It should be noted that the direction "proximal" is defined as the direction in which a urinary catheter 30 is withdrawn from the main body 22. Preferably, first part 26$a$ has a first inner diameter which is less than second inner diameter of second part 26$b$, and third part 26$c$ has a third inner diameter which is less than second inner diameter of second part 26$b$. In other words, the middle second part 26$b$ has a larger diameter than either of the proximal or distal parts.

Figure 2:
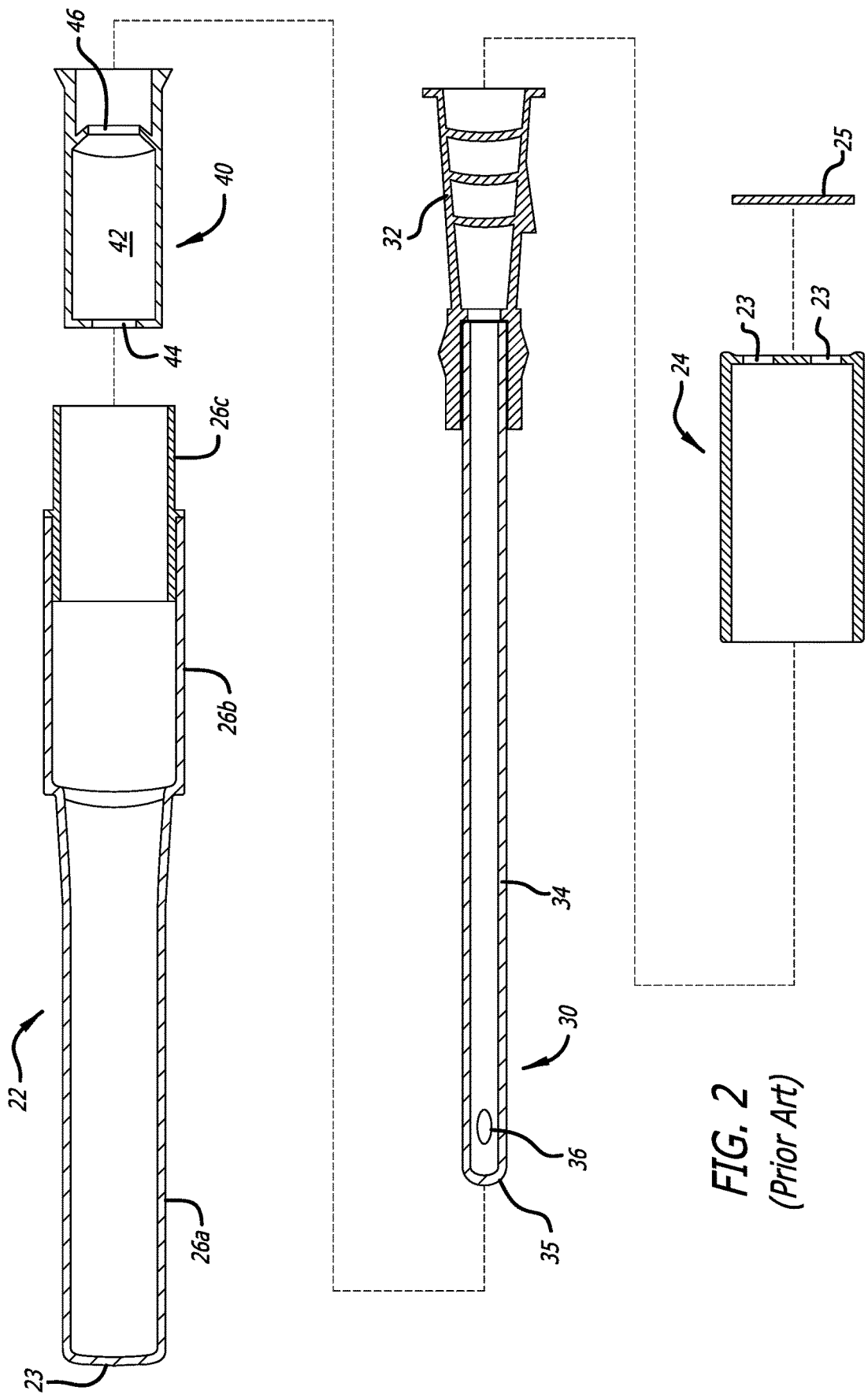
FIG. 2 is an exploded view of the components thereof.

The main body 22 is desirably an assembly of a long distal portion with a shorter tubular connector (that forms the third part 26$a$) bonded thereto for ease of molding (see FIG. 2). The rigid cap 24 can be attached to the connector 26$a$ of the main body 22 using various attachment/locking methods, such as a screw thread, a bayonet closure or a clamping arrangement. The cap 24 desirably has a plurality of openings (not shown) to permit the introduction of a sterilizing gas into the catheter package.

As illustrated, the urinary catheter 30 is stored in a sterile condition within the main body 22 with the cap 24 on. At a proximal end thereof, catheter 30 is provided with a catheter outlet 32 having a throughbore, which may be used as an outlet funnel or as a connector to attach the catheter 30 to a collection bag or other collection device. Catheter 30 includes a flexible catheter tube 34 provided with a rounded tip 35 on a distal end and one or more flow openings 36 proximate the tip. The catheter tube 34 has a lumen in fluid communication with the throughbore of the outlet 32. Openings 36 are provided with rounded and or polished edges 38, such that the entry of urinary catheter tube 34 into the urethral tract of a patient is as comfortable as possible for the patient. The first part 26a of the main body receives the cap 24, the second part 26b holds a gel receptacle 40, and the third part 26c holds the elongated catheter tube 34 of the catheter 30.

The rigid nature of the container 20 and short length of the catheter 30 therein make the sterile package formed by the assembly highly portable and conveniently stored in a purse or even pocket.

The cap 24 contains the proximal outlet 32 of the catheter 30 and may be made of a transparent material, which allows inspection of the outlet 32 (which can, e.g., show size or other indicia, markings, etc.). To facilitate gas sterilization of the components inside the main body 22 with the cap 24 attached, cap 24 is provided with one or more openings 23 that are sealed off with filter element 25, e.g. in the form of a paper or other porous element. For instance, a spun bonded polyolefin material (sold under the tradename Tyvek) may be used which can be heat welded to the cap 24 to provide a seal. After assembling the main body 22 (including bonding the connector 26c), gel container 40, catheter 30 and cap 24, the internal elements of the package are sterilized by introducing a gas such as ethylene oxide through the one or more openings 23 in cap 24.

The dimensions of container 20 (or more specifically, the internal dimensions of main body 22 and cap 24) are adapted to allow storage of the entire catheter 30 (which may have varying dimensions). A length of the container 20 desirably corresponds closely to the length of catheter 30, and is preferably slightly greater than the length of catheter 30 so that the package closely surrounds the entire catheter 30. In accordance with embodiments, catheter 30 can have a length in a range of between about 10-15 cm, which makes catheter 30 especially suited for use with female patients.

The gel receptacle 40 is provided and positioned in second part 26b of main body 22. Gel receptacle 40 is illustrated as a single generally tubular element provided with a cavity 42 in which an amount of a gel-like lubricant agent G is stored. As seen in FIG. 2, gel receptacle 40 includes distal opening 44 at a distal end thereof, and proximal opening 46 at a proximal end thereof. Distal opening 44 has a diameter corresponding generally to outer diameter of catheter tube 34, while proximal opening 46 has a diameter slightly greater than the outer diameter of catheter tube 34. The distal and proximal openings 44, 46 are aligned with each other along a longitudinal centerline 50 extending between the distal and proximal ends of the gel receptacle 40. When taking or otherwise removing catheter 30 in a proximal direction out of the package (to the right in FIG. 1), a layer of the gel-like lubricant extrudes through proximal opening 46 and is deposited on the outside surface of the catheter for use.

Figure 3:
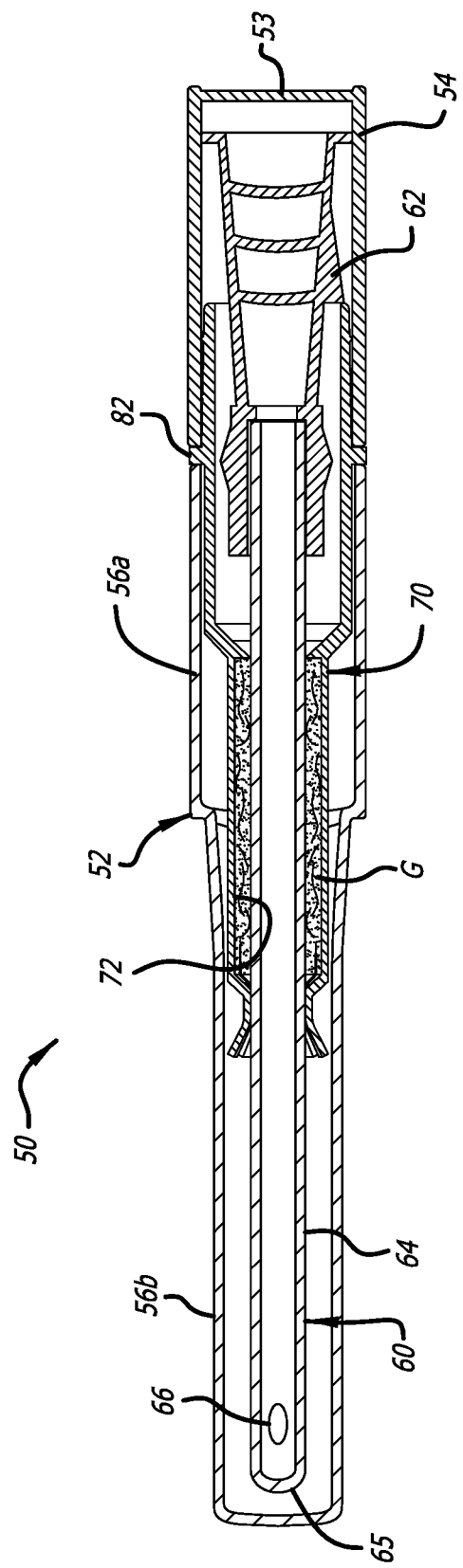
FIG. 3 is a longitudinal sectional view through a sterile container for an intermittent urinary catheter of the present application.

FIG. 3 is a longitudinal sectional view through a sterile container 50 for an intermittent urinary catheter of the present application, FIG. 4 is an exploded view of the components thereof, and FIGS. 5A-5E are perspective and other views of a gel receptacle used in the sterile container. The sterile container 50 is utilized in much the same manner as the container 20 described above, but is constructed and assembled in a more straightforward and less costly manner.

The sterile catheter container 50 includes a pen-like, rigid and generally hollow tubular main body 52 which is closed off at a distal end, and which can be closed off at a proximal, open end using cap 54. The rigid cap 54 can be attached to the main body 52 using various attachment/locking methods, such as a screw thread, a bayonet closure or a clamping arrangement. The end 53 of the cap 54 is solid and closes off the proximal open end of the main body 52 to prevent the introduction of air or other contaminants into the hollow interior of the catheter package. Sterilization prior to shipping is accomplished using gamma rays or an electron-beam.

The cross-sectional view of main body 52 shows a proximal first section 56a and a distal second section 56b. Preferably, proximal section 56a has a first inner diameter which is greater than a second inner diameter of distal section 56b. Both sections 56a, 56b are generally tubular to as to define cylindrical hollow interiors.

As illustrated, with the cap 54 on, a urinary catheter 60 is stored in a sterile condition within the main body 52. At a proximal end thereof, catheter 60 is provided with a catheter outlet 62, which may be used as an outlet funnel or as a connector to attach the catheter 60 to a collection bag or other collection device. Catheter 60 includes a flexible catheter tube 64 provided with a rounded tip 65 on a distal end and one or more flow openings 66 proximate the tip. Openings 66 are provided with rounded and or polished edges, such that the entry of urinary catheter tube 64 into the urethral tract of a patient is as comfortable as possible for the patient.

The rigid nature of the container 50 and short length of the catheter 60 therein make the sterile package formed by the assembly highly portable and conveniently stored in a purse or even pocket, as it resembles a standard item of cosmetics such as eyeliner.

An elongated gel receptacle 70 is provided and positioned in the main body 52. The tube 64 of the urinary catheter 60 extends through the entire gel receptacle 70 such that the distal tip 65 is within the hollow interior of the main body 52.

Gel receptacle 70 is illustrated as a single generally tubular molded polymer element provided with a distal inner cavity 72 in which an amount of a gel-like lubricant agent is stored. As seen in FIG. 4, gel receptacle 70 includes distal opening 74 at a distal end thereof, and proximal opening 76 at a proximal end thereof. Distal opening 74 has a diameter corresponding generally to an outer diameter of catheter tube 64, while proximal opening 76 has a diameter slightly greater than the outer diameter of catheter tube 64. The distal and proximal openings 74, 76 are aligned with each other along a longitudinal centerline 50 extending between the distal and proximal ends of the gel receptacle 70. When the cap 54 is removed the proximal outlet 62 projects out of the gel receptacle 70 so as to be graspable. When removing catheter 60 in a proximal direction out of the package (to the right in FIG. 3), a layer of the gel-like lubricant extrudes through proximal opening 76 and is deposited on the outside surface of the catheter tube 64 for use.

As seen best in FIGS. 5A-5E, the gel receptacle 70 comprises three generally tubular sections: a proximal section 80a, a middle section 80b, and a distal section 80c. The inner cavity 72 is formed exclusively within the distal section 80c. The proximal and middle sections 80a, 80b are generally coextensive and of the same diameter, and are delineated by an outer circumferential rib 82. The distal section 80c is of a smaller diameter than the proximal and middle sections 80a, 80b, and separated therefrom by a tapered shoulder 83.

As seen in FIG. 3, the gel receptacle 70 inserts into the open proximal end of the rigid main body 52 such that the smaller diameter distal section 80c reaches a short distance into the distal section 56b of the main body 52. The middle section 80b has an outer diameter similar to an inner diameter of the proximal section 56a of the main body 52, while the outer circumferential rib 82 is sized the same as the proximal section 56a so as to provide a stop preventing further advancement of the gel receptacle 70 into the container main body 52. The proximal section 80a extends out of the main body 52 and provides a tubular receiver for the cap 54, as will be described. During assembly, the gel receptacle 70 may be secured in this partially inserted position using adhesives, for example, between the exterior of the middle section 80b and the interior of the proximal section 56a of the main body 52.

Figure 5A:
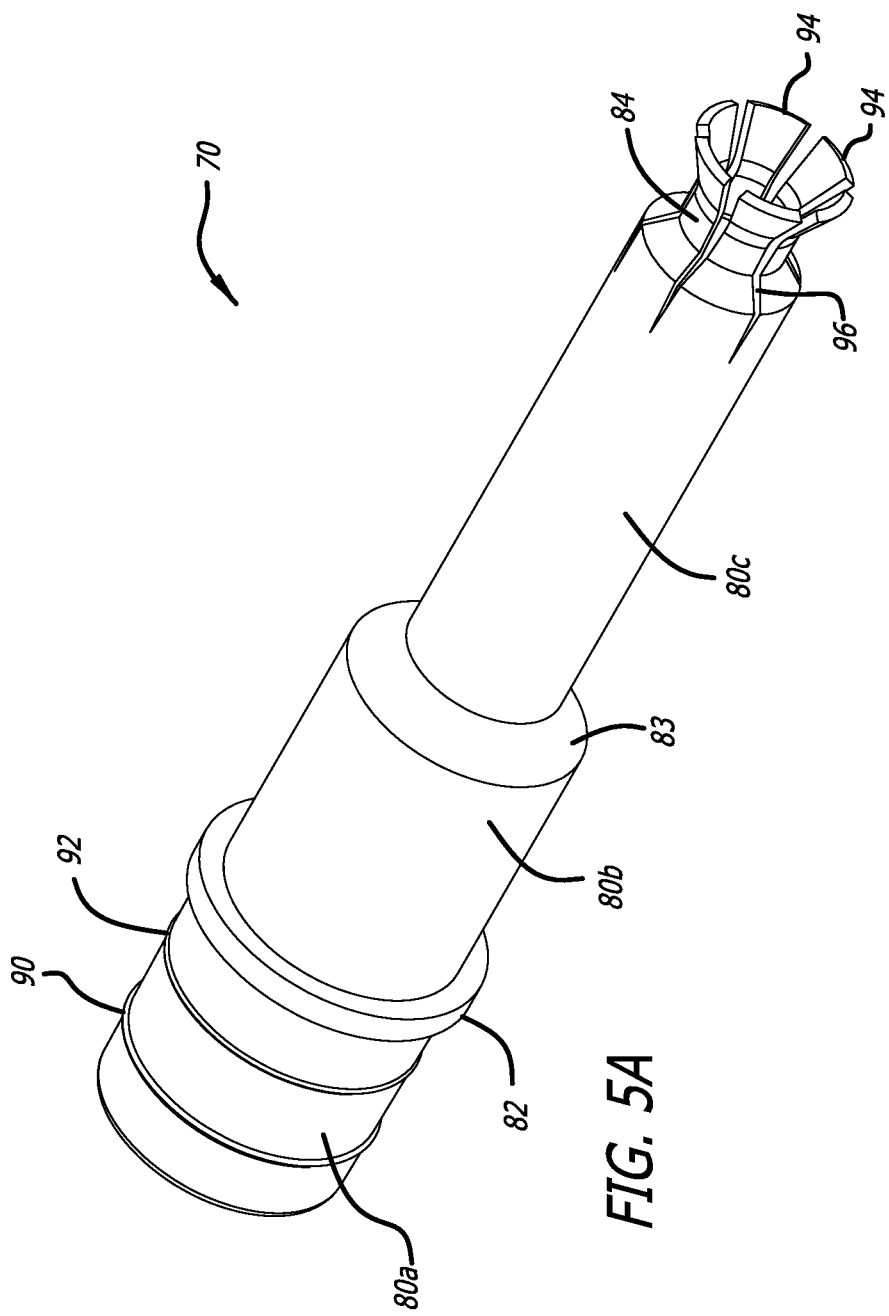
FIG. 5A is a perspective view of a gel receptacle used in the sterile container of FIG. 3, and FIGS. 5B-5E are sectional and interviews thereof.

Namely, the proximal section 80a features two circumferential ribs 90, 92, as seen in FIGS. 5A-5D. The nominal outer diameter proximal section 80a is approximately the same as an inner luminal diameter of the tubular portion of the cap 54, while the ribs 90, 92 are larger and interfere with the cap so as to retain and seal it on the proximal section. As seen in the enlargements of FIGS. 5C and 5D, the ribs 90, 92 are slightly different, with the proximal rib 90 being larger, and the distal rib 92 being slightly smaller, though both are asymmetric in cross-section. In particular, the ribs 90, 92 have a steeper proximal face than a distal face, which helps to facilitate removal of the cap 54 when desired. The less steep distal face gives more support to the proximal face during cap assembly to prevent the rib from rolling. The ribs 90, 92 needs to "shear" at the apex to create an airtight seal between cap and body. The proximal rib is sized larger due to the draft (taper) that narrows toward the proximal opening 86 needed to mold the proximal section 80a. The size difference keeps the top of the ribs at the same plane to meet the cap which has an inner lumen molded with no draft (cylindrical).

The cap 54 surrounds the proximal outlet 62 of the catheter 60 and may be made of a transparent material, which allows inspection of the outlet 62 (which can, e.g., show size or other indicia, markings, etc.). To prevent contamination of the components inside the main body 52 with the cap 54 attached, cap 54 is solid with no openings, in contrast to the Twist catheter which has a porous cap. After assembling main body 52, gel container 70, catheter 60 and cap 54, and adding gel to the gel container 70, the internal elements of the package are sterilized by exposure to gamma rays or an electron-beam.

The dimensions of container 50 (or more specifically, the internal dimensions of main body 52 and cap 54) are adapted to allow storage of the entire catheter 60 (which may have varying dimensions). A length of the container 50 desirably corresponds closely to the length of catheter 60, and is preferably slightly greater than the length of catheter 60 so that the package closely surrounds the entire catheter 60. In accordance with embodiments, catheter 60 can have a length in a range of between about 10-15 cm, which makes catheter 60 especially suited for use with female patients. The entire container 50 preferably has a length of no more than 1-2 cm longer than the catheter 60. So, a 10 cm long catheter would be packaged in a container 50 of between 11-12 cm, and a 15 cm long catheter would be packaged in a container 50 of between 16-17 cm.

As mentioned, inner cavity 72 of gel receptacle 70 includes distal opening 74 at a distal end thereof, and proximal opening 76 at a proximal end thereof. It should be understood that these openings are at the ends of the distal section 80c within which is defined the inner cavity 72.

The overall gel receptacle 70 has a distal end 84 and a proximal end 86. As seen in FIG. 5A, the distal end 84 is defined by a plurality of cantilevered fingers 94 separated by longitudinal slots 96. The slots 96 commence along the distal section 80c and gradually widen toward the distal end of the fingers 94. With reference to the sectional view of FIG. 5B, the distal end 84 formed by the fingers 94 is molded to constrict the distal end of the distal section 80c, then extend a short linear distance within which is defined the distal opening 74, before flaring outward to the distal end of the fingers 94. As stated, the distal opening 74 has approximately the same diameter as the outer diameter of the catheter tube 64 and as such makes surrounding contact therewith to hold the gel within the inner cavity 72. The cantilevered fingers 94 are molded of a flexible polymer which permits introduction of the lubricant gel into the cavity 72 by inserting a syringe or other such implement between the catheter tube 64 and fingers 94, which flex outward.

By comparing the cross-sections of FIGS. 1 and 3 and respective exploded views of FIGS. 2 and 4, certain distinct advantages between the containers 20, 50 are apparent. First of all, aside from the catheter 60 itself, there are only three molded components in the sterile container 50 as compared with four components with the prior art container 20. Similarly, the gel container 40 of the prior art must be forced into the cavity in the middle part 26b and then filled with gel through the open end of the main body 22 before the catheter 30 is inserted, a dual-action operation that is somewhat exacting and thus time-consuming and expensive. Conversely, the catheter 60 of the present container 20 is first inserted through the gel container 70, and then gel is inserted past the flexible fingers 94 and into the inner cavity 72. This gel-filled assembly is then directly inserted into the rigid main body 52 until the circumferential rib 82 contacts the rear end of the proximal section 56a. Finally, the catheter package described herein is completed by adding the cap 54, while the prior art cap 24 must first be combined with the filter element 25, adding another manufacturing step.

In short, the manufacturing advantages of the present container 50 are significant and reduce the costs in a meaningful way in a product whose profit margins are relatively thin to start with. Profit margins are low due to federal government oversight on reimbursement levels for this product. Once the government sets a reimbursement rate, other insurers quickly set their rates at 60-85% of the govt rate. The improved design also lends itself to automation which the prior art design does not mainly due to the difficulty of filling gel once the gel holder is assembled to the tube. This reduces manufacturing costs, which although slight, has a disproportionate impact on profit.

Figure 6:
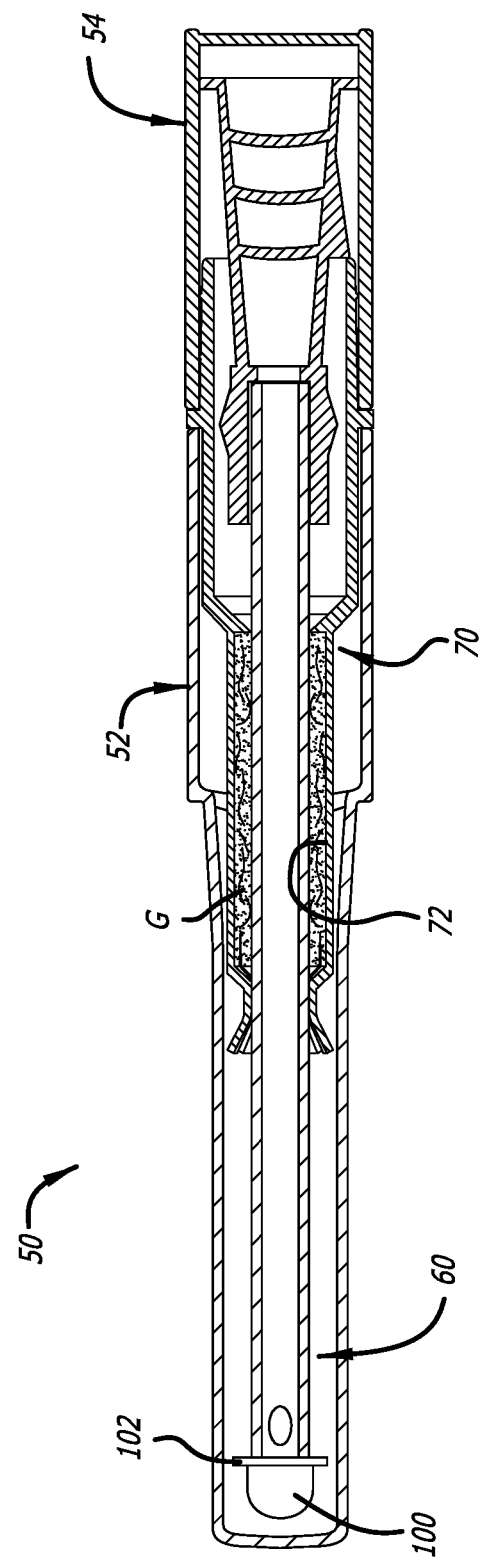
FIG. 6 is a longitudinal sectional view through a sterile container for an intermittent urinary catheter similar to that shown in FIG. 3, and with the addition of a gel cap for the catheter tube.

FIG. 6 is a longitudinal sectional view through the sterile container 50 for an intermittent urinary catheter with the addition of a gel cap 100 for the catheter 60, and FIGS. 7A-7D show several steps in removal of the catheter tube from within the rigid container 50, with the end result being complete coverage of the catheter tube with lubricant gel G.

In some cases, removal of the catheter 60 from within the container 50 may not completely cover the distal tip of the catheter tube with gel, resulting in a dry tip which may hinder introduction into the urethra. Consequently, the gel cap 100 is provided. The gel cap 100 includes a hemispherical cup filled with gel that fits over the distal tip of the catheter 60. The gel cap 100 may be added after the catheter 60 is assembled with the gel container 70 as described above, and preferably after filling the inner cavity 72 with gel. The gel cap 100 remains stuck on the end of the catheter 60 during shipping and handling of the container 50 by the customer by virtue of the viscosity of the gel inside.

Figure 7A:
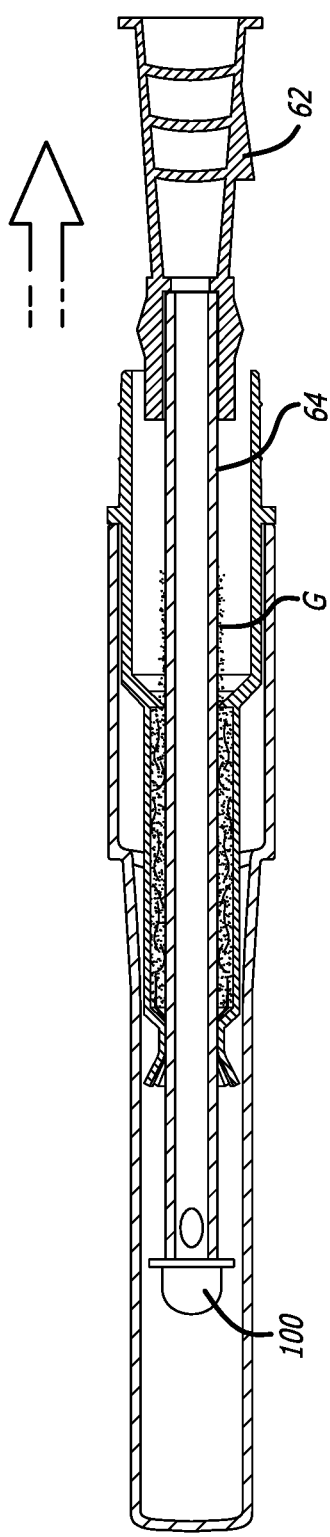
FIGS. 7A-7D show several steps in removal of the catheter tube from within the rigid container shown in FIG. 6, with the end result being complete coverage of the catheter tube with lubricant gel.
Figure 7B:
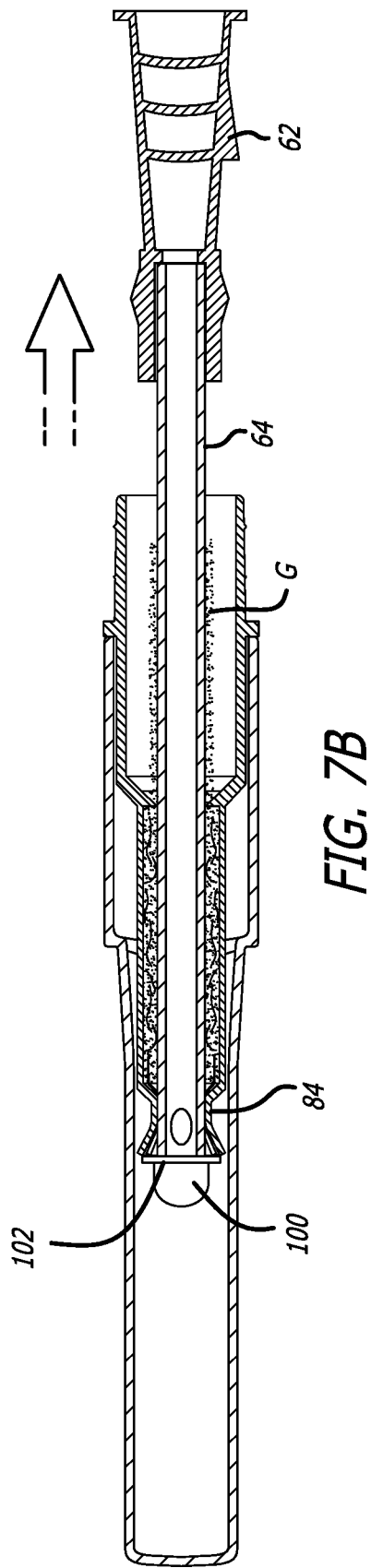
Figure 7C:
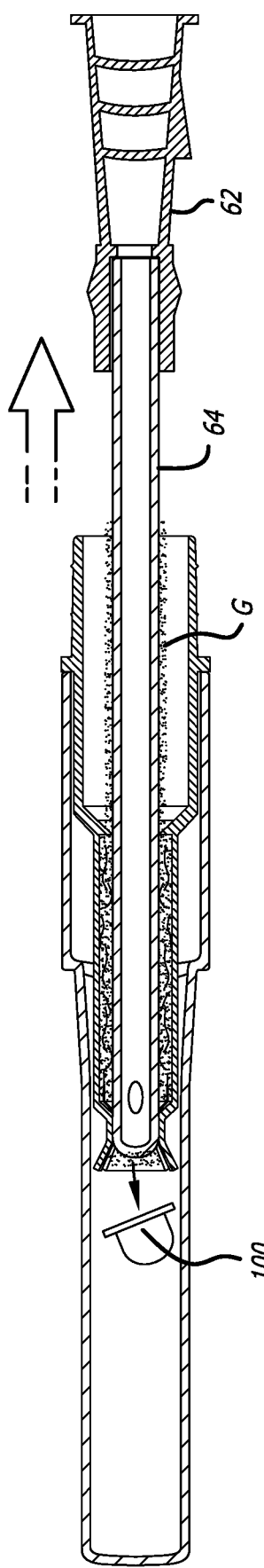
Figure 7D:
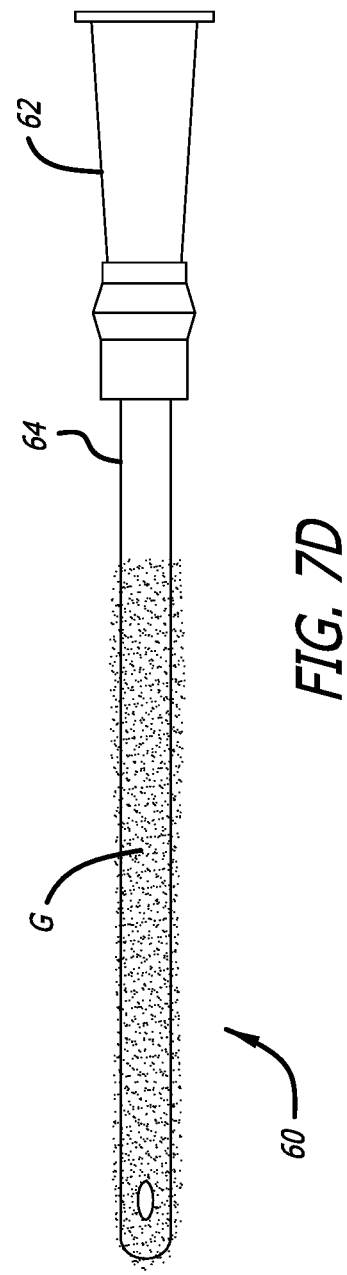

FIGS. 7A-7D show several steps in removal of the catheter 60 from the container 50. As the catheter tube 64 slides out of the gel container 70, gel G coats the outer surface thereof. At the position shown in FIG. 7B, a circular flange 102 on a proximal end of the gel cap 100 contacts the distal end 84 of the gel container 70 within the main body 52. Further withdrawal of the catheter 60 causes the gel cap 100 to fall off the end of the tube 64, as seen in FIG. 7C. Gel G coats the end of the tube 64. Finally, after complete withdrawal, the distal end catheter tube 64 is totally coated with gel G on the distal end and for most of its length. This facilitates introduction into the urethra, and eliminates the occasional problem of a dry tip.

Figure 8B:
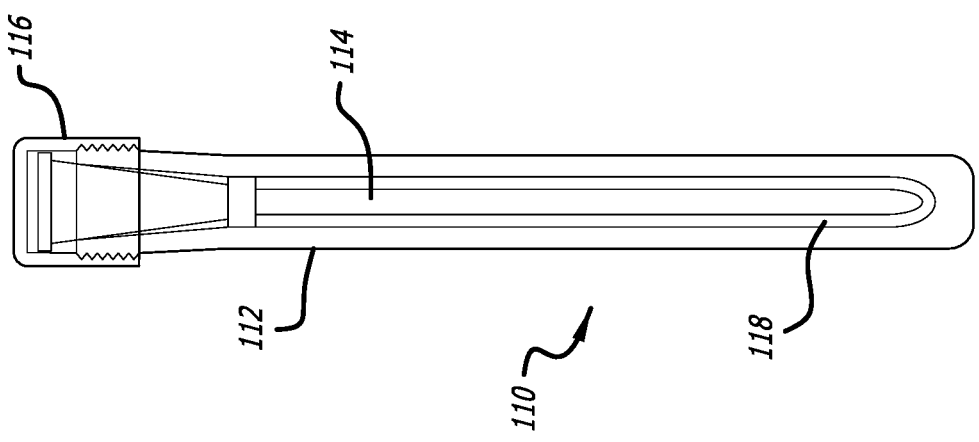
FIGS. 8A-8B are side elevational views of two different sterile containers for intermittent urinary catheters.
Figure 8A:
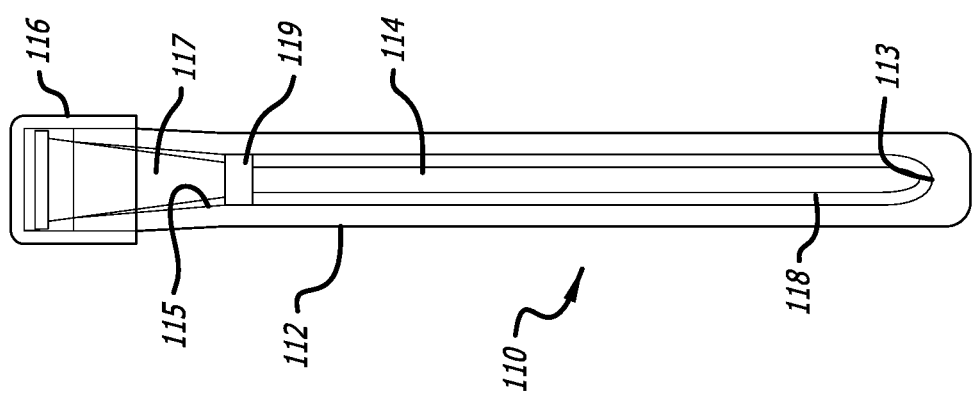

FIGS. 8A-8B are side elevational views of two different sterile containers 110 for intermittent urinary catheters. The two containers 110 are identical except for different cap closures. The containers 110 include a generally tubular main body 112 having a lower closed end opposite an upper open end. A closed cap 116 engages the upper open end of each main body 112 to seal the interior thereof. In FIG. 8A, the cap 116 engages the main body through friction or with interfering ribs, as described above, while in FIG. 8B the cap 116 has a series of internal threads which engage external threads on the mouth of the main body.

The tube of the catheter 114 extends down into the hollow interior defined within each of the main bodies 112. The tube is smaller than the inner diameter of the hollow interiors so as to form concentric spaces 118 therebetween. A lubricating gel (not shown) is provided within the spaces 118 prior to insertion of the catheter 114, such that when the user removes the catheter it is gel coated and ready for use. It should be noted that the inner lumen of the main body 112 is substantially cylindrical down to a rounded dead end 113, but has a tapered upper portion 115 opening to the upper mouth. The catheter 114 has a tapered outlet or funnel 117 which fits closely within the upper portion 115. Additionally, an elastomeric seal or collar 119 is provided at the bottom of the funnel 117 (and is preferably molded therewith) which is sized to engage the cylindrical portion of the main body lumen. The collar 119 thus seals any gel within the concentric space 118.

Figure 9B:
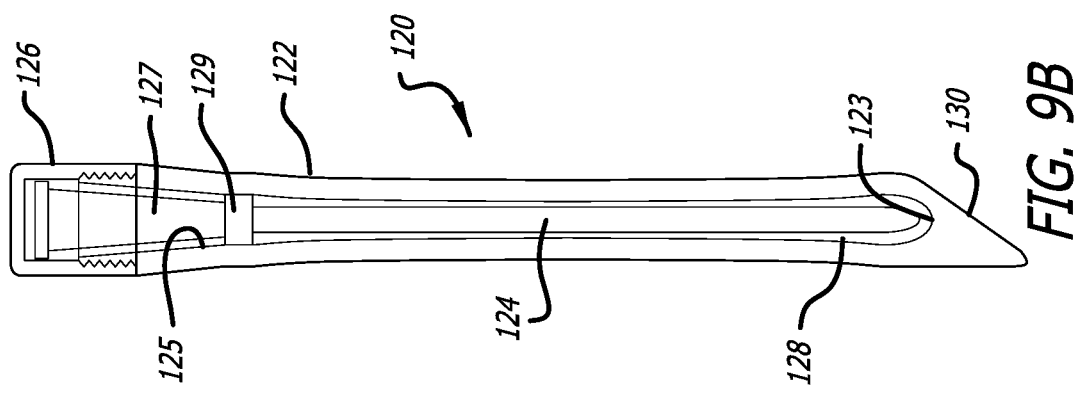
FIGS. 9A-9B are side elevational views of a further sterile container for intermittent urinary catheters.
Figure 9A:
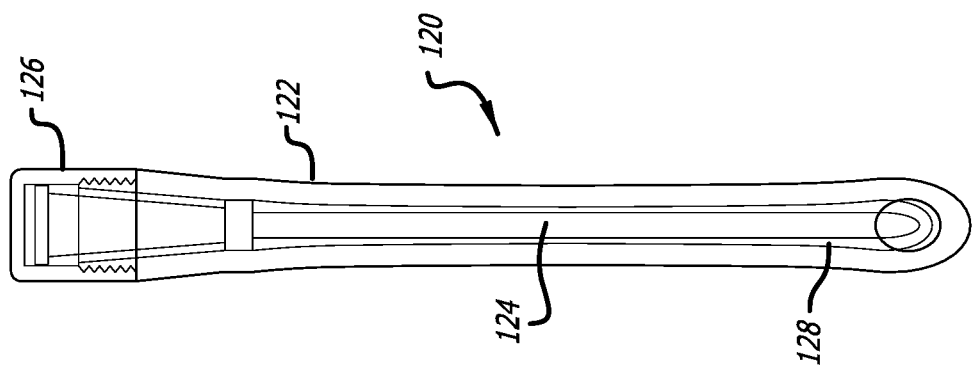

FIGS. 9A-9B are side elevational views of a further sterile container 120 for intermittent urinary catheters. As before, the container 120 includes a generally tubular yet inwardly-tapered main body 122 having a lower closed end opposite an upper open end and a hollow interior. A closed cap 126 engages the upper open end of each main body 122 to seal the interior thereof through friction, with interfering ribs, or with mating threads as shown.

The tube of the catheter 124 extends down into the hollow interior defined within the main body 122. The tube is smaller than the inner diameter of the hollow interior so as to form a concentric space 128 therebetween. A lubricating gel (not shown) is provided within the space 128 prior to insertion of the catheter 124, such that when the user removes the catheter it is gel coated and ready for use. The inwardly-tapered main body 122 and inner space 128 constrict in the middle portion and the lubricating gel is deposited only in the distal end of the hollow interior of the main body 122 which helps reduce the amount of gel that is removed upon catheter removal, thus helping to reduce mess. It should be noted that the inner lumen of the main body 122 has a shallow hourglass shape down to a rounded dead end 123, but has a tapered upper portion 125 opening wider to the upper mouth. The catheter 124 has a tapered outlet or funnel 127 which fits closely within the upper portion 125 and is in fluid communication with the catheter lumen. Additionally, an elastomeric seal or collar 129 is provided at the bottom of the funnel 127 (and is preferably molded therewith) which is sized to engage the narrowing portion of the main body lumen. The collar 129 thus seals any gel within the concentric space 128. The main body 122 further includes an angled distal end 130 through which the distal tip of the catheter 124 can be viewed. The angled distal end 130 may also be squared off, depending on manufacturing constraints.

FIG. 10 is a side elevational view of a still further sterile container 140 for an intermittent urinary catheter. The outer components of the container 140 include a tapered main body 142 which may be closed by a cap 144, such as with mating threads. FIG. 11 is a sectional view of a catheter having an outlet 150 on the proximal end of a catheter tube 152 which is inserted within a generally tubular gel receptacle 154 with a closed distal end. The assembly of the gel receptacle 154 and catheter is seen placed within the hollow interior of the main body 142 of the container 140 in FIG. 10. In a preferred embodiment, the gel receptacle 154 has a tapered configuration which fits closely within the tapered main body 142. An outwardly projecting circular flange 156 at the top of the tapered gel receptacle 154 is sized to contact the gradually narrowing inner walls of the main body 142 in an interference fit so as to secure the gel receptacle within the main body. Alternatively, the flange 156 may be forced past a small inward circular rib (not shown) within the gel receptacle 154 to ensure the gel receptacle 154 remains within the main body 142.

The circular flange 156 defines a central opening through which the catheter tube 152 is inserted into an inner cavity of the gel receptacle. An annular seal or collar 157 at the base of the catheter outlet 150 that is larger than the central opening helps maintain the gel G within the cavity of the gel receptacle 154. As with certain other embodiments described herein, a concentric space is provided around the catheter tube 152 within the inner space which may be filled with lubricant gel G. The central opening in the circular flange 156 has an inner diameter A, shown in FIG. 11A which is slightly larger than the outer diameter D of the catheter tube 152. When the user withdraws the catheter from within the gel receptacle 154, gel G coats the exterior of the catheter tube 152, as seen in FIG. 12. The spacing created between the catheter tube 152 and the central opening wipes off a majority of the gel G which might otherwise stick to the tube but leaves a thin coating thereon. In one embodiment, the diameter D of the catheter tube 152 ranges between 8-16 French, or between about 2.7-5.3 mm (3 Fr=1 mm). The diameter A of the central opening is desirably about 1-2 mm larger than the corresponding catheter tube diameter, or between 3.7-7.3 mm. Since the entirety of the inner cavity of the gel reservoir 154 is filled with gel G, the distal tip of the catheter to 152 emerges covered with gel as well.

Radial score lines 158 allow for molding of the gel holder 154. There is an undercut design for the flange 156 and the score lines 158 allow for removal of the mold core by allowing the flange to flex open during part ejection.

Figure 14:
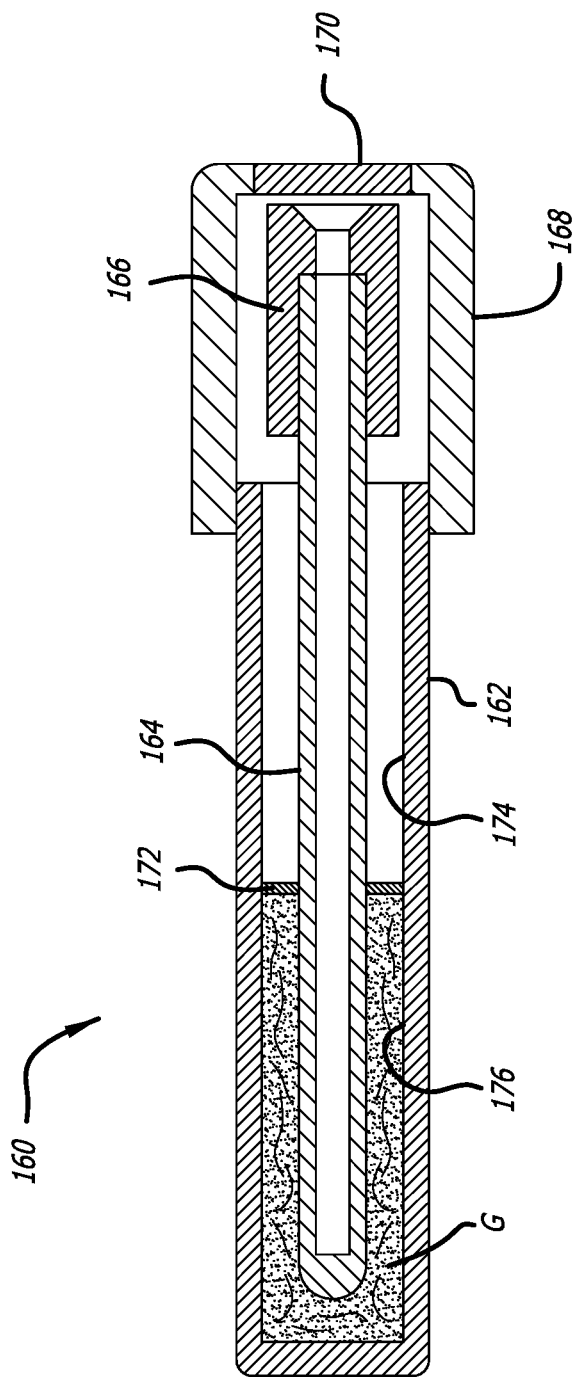
FIG. 14 is a longitudinal sectional view through an alternative sterile container for an intermittent urinary catheter.

FIG. 14 is a longitudinal sectional view through an alternative sterile container 160 for an intermittent urinary catheter. In this version, the container 160 includes a generally tubular main body 162 closed at one end and open at the other. The catheter tube 164 inserts within the open end of the main body 162 such that an outlet 166 remains outside. A cap 168 is then secured around the main body 162 using any of the means described herein. The cap 168 preferably has a solid end 170.

A barrier or divider wall 172 segregates the inner volume of the main body 162 into a proximal first section 174 and a distal second section 176. The divider wall 172 is a central aperture sized slightly larger than the outer diameter of the catheter tube 164, such that the tube is passed through the aperture and a distal portion resides within the second section 176, which may be filled with gel G. The divider wall 172 thus helps retain the gel G in the distal end of the closed main body 162 to reduce mess when withdrawing the catheter. As the catheter is withdrawn, it emerges coated with gel G along its distal length and distal tip. The difference in diameter between the aperture of the divider wall 172 and the outer diameter of the catheter tube 164 may be the same as described above for the gel receptacle 154 of FIG. 11. That is, the diameters A and B may be the same in the embodiment of FIGS. 14 and 14A-14B.

Figure 14A:
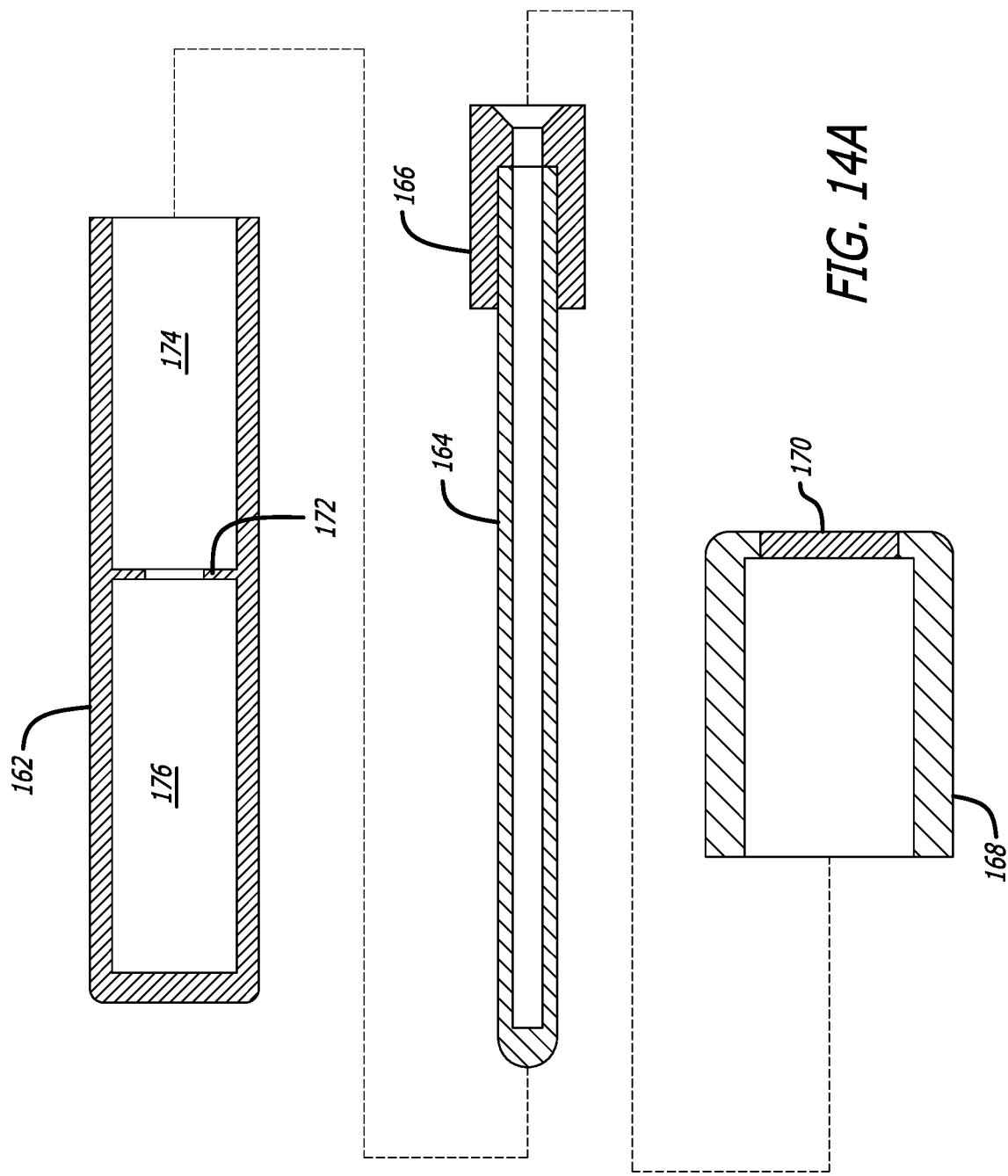

FIGS. 14A-14B are exploded views of alternative confiugrations of the components of the sterile container 160 of FIG. 14. In the first embodiment of FIG. 14A, the divider wall 172 is formed by a molded bulkhead within the main body 162. Conversely, in the embodiment shown in FIG. 14B, the divider wall 172 is a removable annular disk. This embodiment is slightly easier to manufacture, though accommodation must be made to retain the disk 172 within the main body 162. In one embodiment, the annular disk 172 is retained within the inside of the main body 162 with adhesive. In another embodiment the disk is held in place by a snap fit into a ring-shaped receiving cavity.

In each of the embodiments shown in FIGS. 8-14, the catheter can have a length in a range of between about 10-15 cm, which makes the catheter especially suited for use with female patients. The entire container preferably has a length of no more than 1-2 cm longer than the catheter. So, a 10 cm long catheter would be packaged in a container of between 11-12 cm, and a 15 cm long catheter would be packaged in a container of between 16-17 cm.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A urinary catheter package consisting essentially of: a rigid generally tubular main body having a distal closed end and a proximal open mouth, the main body defining within itself a hollow interior;
   a gel receptacle having a distal section defining an inner cavity at least partly filled with a lubricating gel and a proximal section, the distal section having a distal opening and a proximal opening leading to the proximal section, and the proximal section having an open proximal end, wherein the gel receptacle is inserted through the open mouth of the main body and into the hollow interior, the gel receptacle having an outer circumferential rib at one end of the proximal section that is sized to interfere with the open mouth such that the proximal section remains outside the hollow interior of the main body;
   a urinary catheter having an elongated flexible tube defining a closed distal tip with one or more flow openings formed in an adjacent sidewall thereof, and a proximal outlet attached to a proximal end of the tube and having a throughbore in communication with a lumen of the tube, wherein the tube of the urinary catheter is inserted first into the open proximal end of the proximal section and extends through the entire gel receptacle such that the distal tip extends past the distal opening of the distal section and is within the hollow interior of the main body and at least a portion of the outlet remains outside the main body, and wherein a concentric space is formed around the tube within the distal section of the gel receptacle such that lubricating gel remains on the catheter tube when the tube is retracted from within the gel receptacle; and
   a rigid cap secured to the proximal section of the gel receptacle, the rigid cap being solid without openings so as to seal the urinary catheter within the hollow interior in a sterile manner.

2. The urinary catheter package of claim 1, further including a gel cap filled with gel that fits over the distal tip of the catheter tube, the gel cap being larger than the distal opening of the distal section so that it falls off the end of the tube when the tube is retracted from within the gel receptacle.

3. The urinary catheter package of claim 2, wherein the gel cap has a hemispherical cup-shaped body and an outer flange that is larger than the distal opening of the distal section.

4. The urinary catheter package of claim 1, wherein the distal opening of the distal section of the gel receptacle is defined by a plurality of cantilevered fingers separated by longitudinal slots that may be flexed outward, and the gel receptacle is molded of a flexible polymer which permits introduction of the lubricant gel into the inner cavity by inserting a syringe between the catheter tube and the cantilevered fingers which flex outward.

5. The urinary catheter package of claim 4, wherein the longitudinal slots commence along the distal section and gradually widen toward distal ends of the cantilevered fingers.

6. The urinary catheter package of claim 4, wherein the cantilevered fingers are molded to constrict a distal end of the distal section, then extend a short linear distance within which is defined the distal opening, before flaring outward to distal ends of the cantilevered fingers.

7. The urinary catheter package of claim 1, wherein the catheter has a length of between about 10-15 cm, and the catheter package has a length of no more than 1-2 cm longer than the catheter.

8. The urinary catheter package of claim 1, wherein the proximal section of the gel receptacle has a diameter that is approximately the same as an inner luminal diameter of the rigid cap such that the rigid cap is secured to the proximal section with an interference fit.

9. The urinary catheter package of claim 8, wherein the proximal section has a pair of external axially-spaced ribs that interfere with the inner luminal diameter of the rigid cap so as to retain and seal it on the proximal section.

10. The urinary catheter package of claim 9, wherein the proximal section is molded with a slight narrowing taper toward the proximal opening and a proximal rib is sized larger than a distal rib so as to have about the same diameter as the distal rib.

11. The urinary catheter package of claim 9, wherein the ribs are triangular and asymmetric in cross-section with a steeper proximal face than a distal face.

12. A urinary catheter package, comprising: a rigid generally tubular main body having a distal closed end and a proximal open mouth, the main body defining within itself a hollow interior;
- a gel receptacle having a distal section defining an inner cavity at least partly filled with a lubricating gel and a proximal section, the distal section having a distal opening and a proximal opening leading to the proximal section, and the proximal section having an open proximal end, wherein the gel receptacle is inserted through the open mouth of the main body and into the hollow interior, wherein the gel receptacle is molded of a flexible polymer and the distal opening of the distal section of the gel receptacle is defined by a plurality of cantilevered fingers separated by longitudinal slots that may be flexed outward, wherein the cantilevered fingers are molded to constrict a distal end of the distal section, then extend a short linear distance within which is defined the distal opening, before flaring outward to distal ends of the cantilevered fingers;
- a urinary catheter having an elongated flexible tube defining a closed distal tip with one or more flow openings formed in an adjacent sidewall thereof, and a proximal outlet attached to a proximal end of the tube and having a throughbore in communication with a lumen of the tube, wherein the catheter has a length of between about 10-15 cm, wherein the tube of the urinary catheter is inserted first into the open proximal end of the proximal section and extends through the entire gel receptacle such that the distal tip extends past the distal opening of the distal section and is within the hollow interior of the main body and at least a portion of the outlet remains outside the main body, wherein the gel receptacle permits introduction of a lubricant gel into the inner cavity by inserting a syringe between the tube of the catheter and the cantilevered fingers of the gel receptacle which flex outward, and wherein a concentric space is formed around the tube within the distal section of the gel receptacle such that lubricating gel remains on the catheter tube when the tube is retracted from within the gel receptacle; and
- a rigid cap secured to the proximal section of the gel receptacle, the rigid cap being solid without openings so as to seal the urinary catheter within the hollow interior in a sterile manner.

13. The urinary catheter package of claim 12, further including a gel cap filled with gel that fits over the distal tip of the catheter tube, the gel cap being larger than the distal opening of the distal section so that it falls off the end of the tube when the tube is retracted from within the gel receptacle.

14. The urinary catheter package of claim 13, wherein the gel cap has a hemispherical cup-shaped body and an outer flange that is larger than the distal opening of the distal section.

15. The urinary catheter package of claim 12, wherein the longitudinal slots commence along the distal section and gradually widen toward distal ends of the cantilevered fingers.

16. The urinary catheter package of claim 12, wherein the proximal section of the gel receptacle has a diameter that is approximately the same as an inner luminal diameter of the rigid cap such that the rigid cap is secured to the proximal section with an interference fit.

17. The urinary catheter package of claim 16, wherein the proximal section has a pair of external axially-spaced ribs that interfere with the inner luminal diameter of the rigid cap so as to retain and seal it on the proximal section.

18. The urinary catheter package of claim 17, wherein the proximal section is molded with a slight narrowing taper toward the proximal opening and a proximal rib is sized larger than a distal rib so as to have about the same diameter as the distal rib.

19. The urinary catheter package of claim 17, wherein the ribs are triangular and asymmetric in cross-section with a steeper proximal face than a distal face.

* * * * *